United States Patent [19]

Greenfield et al.

[11] Patent Number: 5,393,494

[45] Date of Patent: * Feb. 28, 1995

[54] APPARATUS FOR DRAWING FLUID SAMPLE, COMPONENTS THEREOF, AND SLIDE ASSEMBLY FOR USE THEREWITH

[75] Inventors: Walter Greenfield, Scarsdale, N.Y.; Edward G. Kearns, North Haven; James E. Kemble, Madison, both of Conn.

[73] Assignee: DiaSys Corporation, Waterbury, Conn.

[*] Notice: The portion of the term of this patent subsequent to Sep. 28, 2010 has been disclaimed.

[21] Appl. No.: 48,905

[22] Filed: Apr. 14, 1993

Related U.S. Application Data

[63] Continuation-in-part of Ser. No. 889,630, May 28, 1992, Pat. No. 5,248,480.

[51] Int. Cl.$^6$ ............................................. B01F 11/00
[52] U.S. Cl. .................................... 422/68.1; 422/72; 422/81; 422/100; 73/864.74; 73/864.03; 356/246; 359/398
[58] Field of Search ............... 422/100, 101, 102, 68.1, 422/81, 72; 73/864.03, 864.02, 864.74; 356/246; 359/396, 398

[56] References Cited

U.S. PATENT DOCUMENTS

| | | | |
|---|---|---|---|
| 3,065,669 | 11/1962 | Orsi | 359/398 |
| 3,481,477 | 12/1969 | Farr | 210/359 |
| 3,508,653 | 4/1970 | Coleman | 210/789 |
| 3,512,940 | 5/1970 | Shapiro | 422/101 |
| 3,552,864 | 1/1971 | Shields | 356/246 |
| 3,582,222 | 6/1971 | Hoblik | 356/246 |
| 3,586,064 | 6/1971 | Brown | 141/1 |
| 3,726,597 | 4/1973 | Dvorak et al. | 359/398 |
| 3,814,248 | 6/1974 | Lawhead | 210/789 |
| 3,835,710 | 9/1974 | Pogorski | 73/864.74 |
| 3,841,838 | 10/1974 | Natelson | 422/102 |
| 3,849,072 | 11/1974 | Ayres | 210/789 |
| 3,887,464 | 6/1975 | Ayres | 210/117 |
| 3,888,113 | 6/1975 | Miranda | 73/64.41 |
| 3,894,951 | 7/1975 | Ayres | 210/136 |
| 3,897,343 | 7/1975 | Ayres | 210/516 |
| 3,935,113 | 1/1976 | Ayres | 210/516 |
| 3,941,699 | 3/1976 | Ayres | 210/117 |
| 3,945,928 | 3/1976 | Ayres | 210/516 |
| 3,948,607 | 4/1976 | Atwood et al. | 422/63 |
| 4,037,464 | 7/1977 | Wenander | 73/61.65 |
| 4,055,501 | 10/1977 | Cornell | 210/516 |
| 4,209,256 | 6/1980 | Faulkner | 356/246 |
| 4,271,123 | 6/1981 | Curry et al. | 422/64 |
| 4,302,421 | 11/1981 | Baker | 422/64 |
| 4,308,028 | 12/1981 | Elkins | 422/56 |
| 4,312,591 | 1/1982 | Tomoff | 356/315 |
| 4,320,087 | 3/1982 | Chau et al. | 422/69 |
| 4,367,043 | 1/1983 | Sweet et al. | 356/338 |
| 4,393,466 | 7/1983 | Deindoerfer | 364/415 |
| 4,448,752 | 5/1984 | Banno et al. | 422/81 |
| 4,464,254 | 8/1984 | Dojki et al. | 210/136 |
| 4,569,764 | 2/1986 | Satchell | 210/511 |
| 4,612,614 | 9/1986 | Deindoerfer et al. | 364/415 |
| 4,681,742 | 7/1987 | Johnson et al. | 422/102 |
| 4,804,267 | 2/1989 | Greenfield | 356/335 |
| 4,824,560 | 4/1989 | Alspector | 209/208 |
| 4,836,038 | 6/1989 | Baldwyn | 73/864.21 |
| 4,917,801 | 4/1990 | Luderer et al. | 210/516 |
| 4,981,654 | 1/1991 | Kuntz et al. | 422/102 |
| 4,983,038 | 1/1991 | Ohki et al. | 356/246 |
| 5,248,480 | 9/1993 | Greenfield et al. | 422/68.1 |

Primary Examiner—Robert J. Warden
Assistant Examiner—T. A. Trembley
Attorney, Agent, or Firm—St. Onge Steward Johnston & Reens

[57] ABSTRACT

An apparatus for drawing a specimen of a body fluid, such as urine from a sample tube. The specimen is drawn through a reusable slide assembly for examination. The slide assembly includes a glass enclosure shaped to provide a viewing chamber for use with a microscope. A sample tube with a special plug and ball valve provides a solids collection chamber with which a uniform amount of body liquid is provided for the specimen.

24 Claims, 7 Drawing Sheets

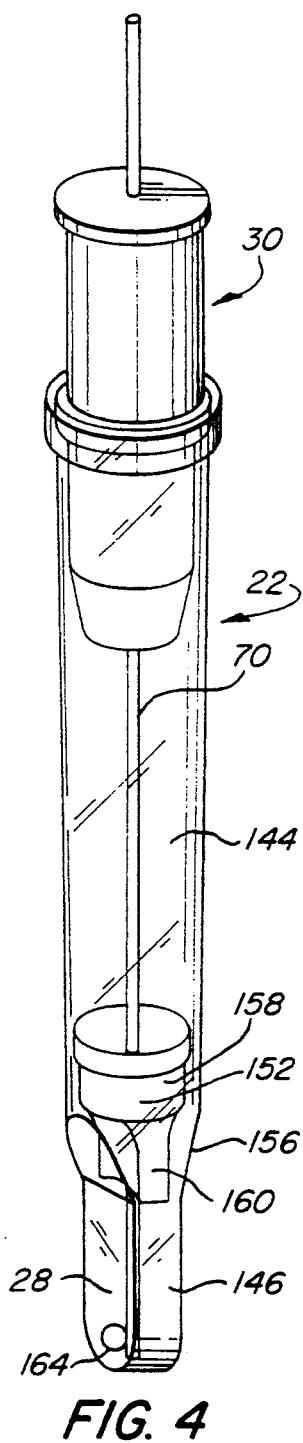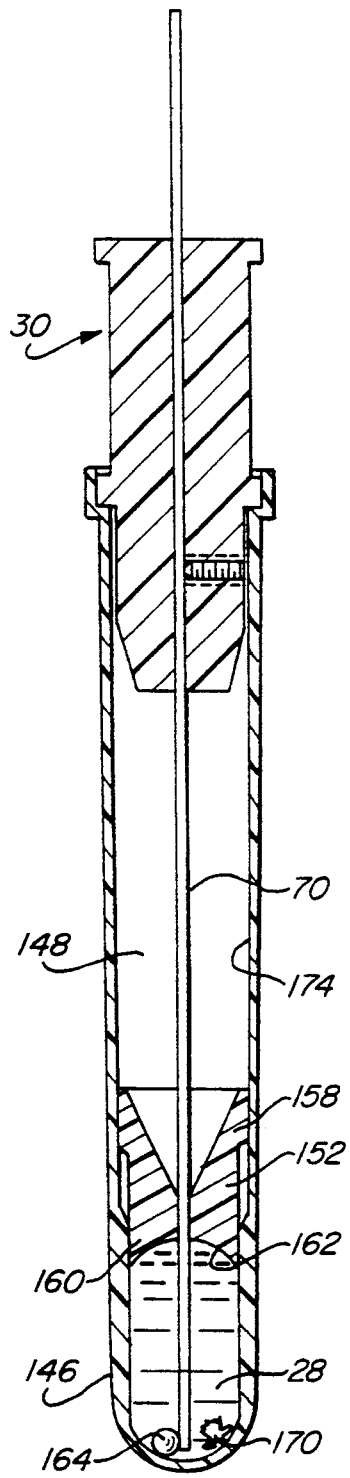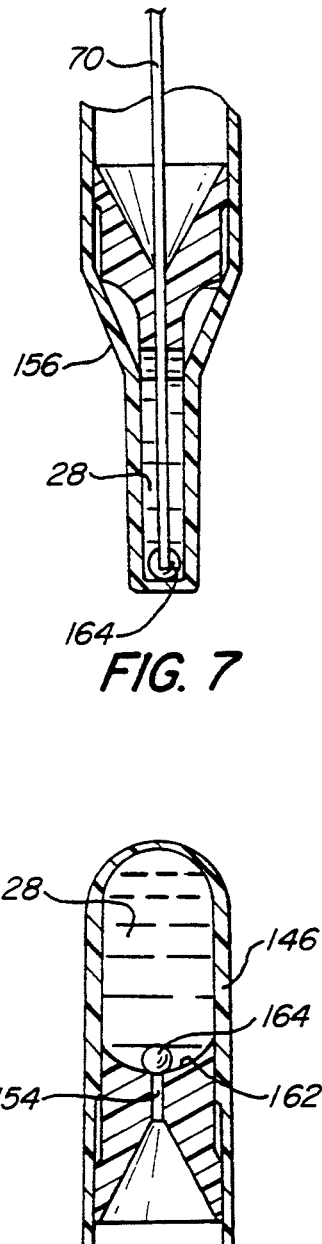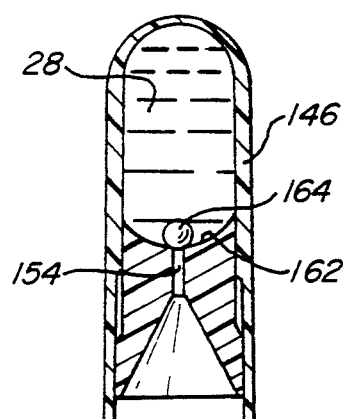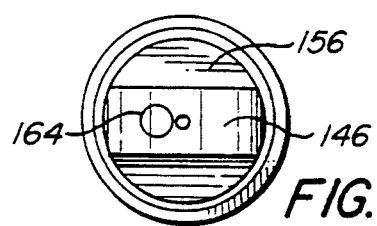

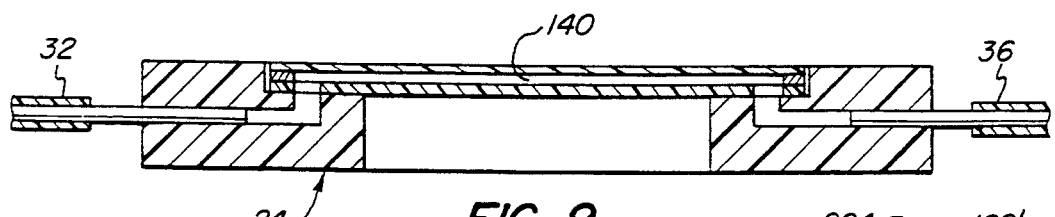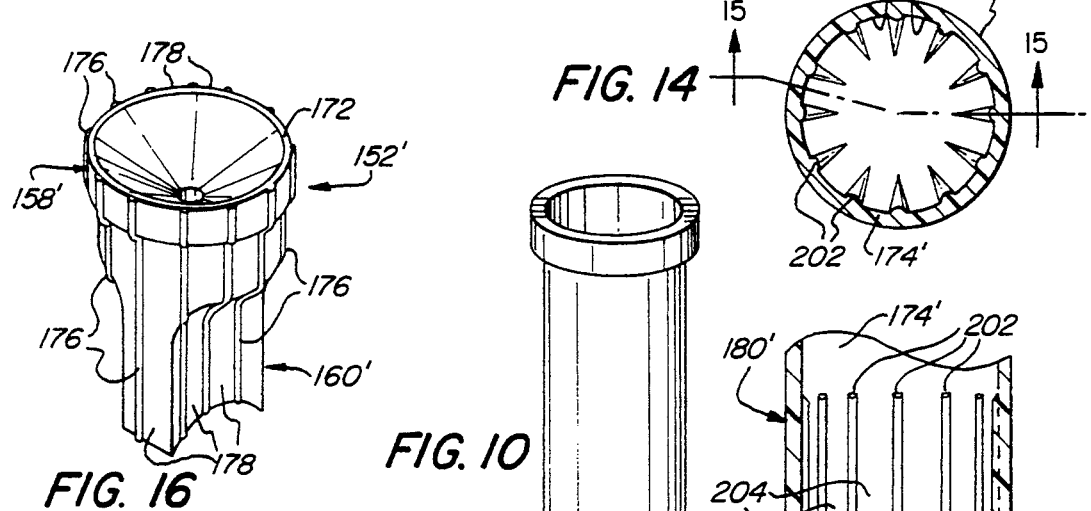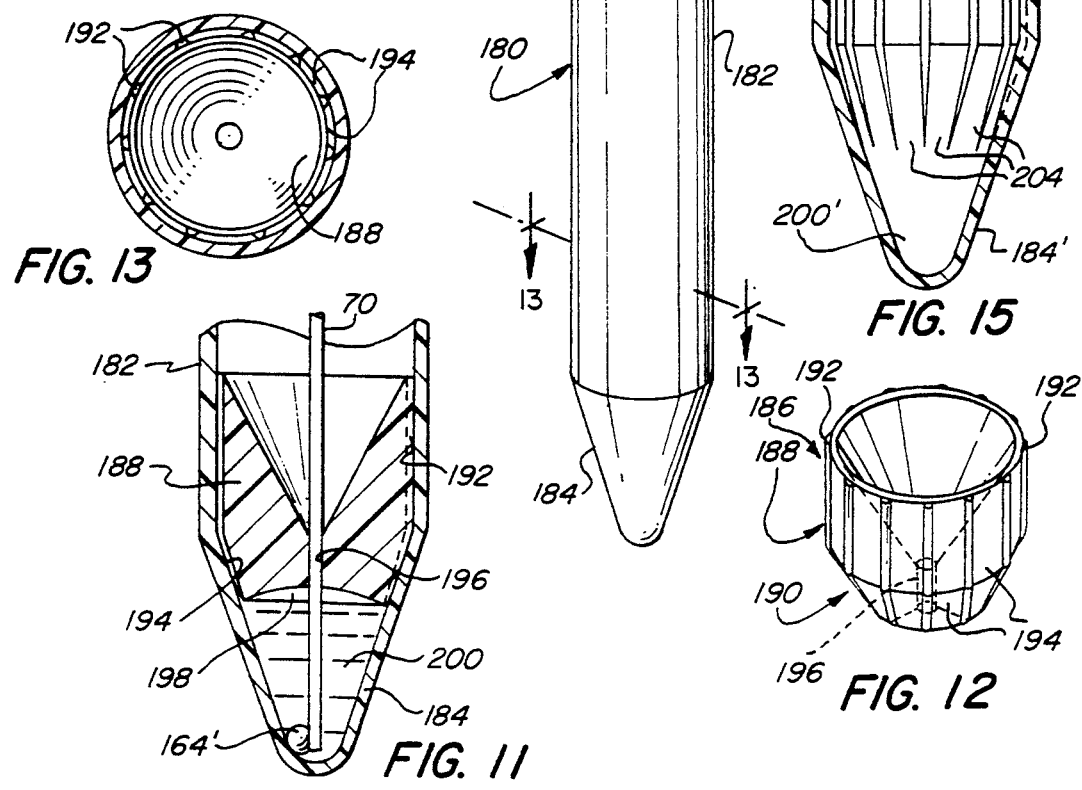

APPARATUS FOR DRAWING FLUID SAMPLE, COMPONENTS THEREOF, AND SLIDE ASSEMBLY FOR USE THEREWITH

PRIOR APPLICATION

This application is a continuation-in-part of U.S. patent application Ser. No. 889,630, filed on May 28, 1992, now U.S. Pat. No. 5,248,480.

FIELD OF THE INVENTION

This invention relates to an apparatus and technique for drawing a fluid specimen sample for analysis from a sample tube into a slide assembly and relates to a sample collection tube for use in such analysis. More specifically, this invention relates to an apparatus and technique for use in a urinalysis and to a slide assembly into which a fluid sample can be conveniently drawn, and after analysis, flushed out.

BACKGROUND OF THE INVENTION

Systems and devices for urinalysis are extensively used and practiced in clinics, laboratories and the like. With the increased presence of infectious diseases, such as AIDS, in biological materials, the need for safe systems and devices to minimize the handling of these potentially dangerous substances becomes evident. Urine sediment examination typically involves, as described in the U.S. Pat. Nos. 4,393,466 and 4,612,614, pouring of a sample into a tube which is then spun in a centrifuge to separate the sediment from its suspending fluid. After centrifugation, the cleared suspending fluid is poured out and the sediment resuspended in the remaining fluid. A sample of the resuspended sample must then be transferred to a microscopic slide for examination with a microscope. The '466 patent further describes a technique with which manual urine handling steps are eliminated and a video system is used to provide an electronic image of the urine specimen. A slide assembly is described which is shaped to provide a stable sample area where solid particles in the urine sample can be viewed.

Various other types of urine or other fluid sample supply devices are shown and described in the art, see for example, U.S. Pat. Nos. 4,302,421, 4,312,591, 4,367,043, 4,448,752, 4,836,038, 3,948,607, 4,209,256, and 4,271,123.

U.S. Pat. No. 4,804,267 to Walter Greenfield describes a urine sample analyzing system. A peristaltic pump is used to alternately pull a urine sample or a flushing fluid through a slide assembly, also known as a flow cell. A video display system is employed to investigate solids in the sample.

Problems encountered with conventional slide assemblies may involve too great a thickness of the test specimen so that the microscope, which usually has a very short focal length, tends to be focused at different focal planes of the test specimen. When the flow cell is made with plastic components through which either the microscope views the test sample or through which illuminating light passes, distortions tend to appear in the field of view of the microscope. Frequently, cement may be used to attach flow cell components and this cement tends to be attacked by constituents in the urine and some cleaning fluids over extended uses leading to a disintegration of the slide assembly. Cement also tends to have tiny edges to which various undesirable contaminants become attached such as bacteria, molds, yeast and particles and are not readily dislodged by a flushing cycle. When the passageway into the viewing chamber of the slide assembly has relatively abrupt turns, tiny bubbles tend to form and are entrained into the viewing chamber where they obscure or confuse the clarity of the field of view of the microscope. Where cement/plastic plexiglass interfaces are exposed to air and heat from the condensed light source, dust particles are attracted and appear as other urine constituents such as bacteria, yeast, fibers, and mucus to the microscope operator when these interfaces also appear in the field of view.

It is important that slide assemblies are sufficiently thin to enable mounting to any microscope without interference with different lenses of a microscope turret. It is also desirable that a slide assembly be useful with a variety of microscopic techniques such as the one commonly known as "bright field" and other techniques generally referred to as Hoffman modulation, phase contrast, polarized light and fluorescence. It is furthermore desirable that a relatively small amount of test fluid is used to fill a viewing chamber of a slide assembly so that more than one examination can be made with the same test fluid.

The various known urinalysis systems tend to be complex and do not provide an inexpensive and convenient approach to the handling of urinalysis in laboratories where complex fully automated systems cannot easily, economically be justified.

In the evaluation of urine, it is at first necessary to concentrate the solids in a centrifuge operation, but then the solids should be resuspended. In order to achieve a reasonably consistent basis for analysis, the resuspension preferably should be carried out with the same volume of urine.

Various collection tubes have been proposed for extracting, separating or otherwise segregating components from a body fluid. For example, U.S. Pat. No. 3,818,248 describes a collection tube with which different phases of a fluid are separated. The device includes a movable sealing element or "traveling spool" which divides a test tube into an upper chamber and a lower chamber which has a floating plug. This device can serve the function described but does not permit the collection of a fixed or constant volume or urine.

U.S. Pat. No. 4,824,560 describes a urine centrifuge tube containing a partition that is shaped to promote the collection of solids in a lower chamber during centrifuge. The partition is pierced by a bore whose cross-section is less than 10 mm. and preferably not more than 5 mm. and is described even as a capillary bore. Even though the tube can yield a collection of solids in a lower chamber, during the decanting of excess liquid from the upper chamber, liquid from the lower chamber would tend to escape as well. This is particularly a problem with larger bore sizes while with a capillary bore, it is difficult to remove a consistent sample. Furthermore, no device is shown to facilitate the break-up for resuspension of consolidated solids.

Other body liquid collection tubes, some for centrifuge operations, are described in U.S. Pat. Nos. 4,464,254, 4,308,028, 4,055,501, 3,935,113, 3,945,928, and 3,849,072. These patents describe devices with similar drawbacks.

SUMMARY OF THE INVENTION

With an apparatus in accordance with the invention, a urine sediment analysis can be performed in a hygienic, efficient, and consistent manner while using an available standard upright microscope and a reusable slide assembly.

This is achieved with one apparatus in accordance with the invention by using a slide assembly that can be irrigated with a flush solution and easily mounted on a microscope, and a compact fluid control device with which a urine sample can be drawn by a pump from a urine collection tube through the slide assembly and subsequently flushed back into the tube with a flushing liquid.

A plurality of urine samples can be rapidly and efficiently sampled in an efficient manner. A housing is provided on which a plurality of special centrifuge tubes are removably mounted for processing. A centrifuged urine sample containing tube is temporarily mounted at a test station where a probe is extended into the tube and into a solids collection chamber where solids have congregated and have been resuspended in a substantially constant volume.

A control is then actuated with which a sample from the solids collection chamber is drawn up through the slide assembly to a place that is between it and the housing for the apparatus of this invention. Upon completion of the microscopic examination, the control is again actuated so that the pump can be reversed and flushing liquid pumped from the reservoir through the slide assembly into the centrifuge tube.

With an apparatus in accordance with the invention, manual exposure to body fluid samples is significantly reduced, a rapid handling and safe examination of samples can be achieved and consistent examination results are achieved.

The consistency is particularly enhanced by maintaining a constant sample holding volume in the centrifuge sample collection tube. This is obtained by employing a plug in a centrifuge tube that is held in a fixed position in the tube so as to define a solids collection chamber between the plug and the closed bottom end of the tube. The plug has a bore through which solids can pass through into the solids collection chamber during a centrifuge operation. The bore terminates in the latter chamber in a valve seat and a loose-fitting valve element is located inside the chamber. The valve element has a sufficiently high specific gravity so that it will not float and solids can pass through the bore into the collection chamber.

However, at the conclusion of the centrifuge operation, the excess fluid can be decanted by inversion of the tube without a significant loss of fluid from the solids collection chamber since the valve element will automatically close the through bore by moving onto the valve seat.

With a submerged valve element loose in the collection chamber, any solid sediments that may have aggregated into a consolidated mass can be conveniently loosened and resuspended throughout the fluid in the collection chamber. This involves a gentle shaking of the tube in a manner whereby the valve element can break up consolidated sediments and resuspend the solids in a substantially constant volume of liquid.

The reliability, versatility, and effectiveness of an apparatus in accordance with the invention is further enhanced by use of a slide assembly with which a urine sample can be drawn and subsequently conveniently viewed through a microscope. The slide assembly also known as a flow cell, is formed with an elongate optical glass enclosure. The enclosure has spaced-apart upper and lower sides which present substantially flat surfaces for examination of a urine sample drawn into a viewing chamber bounded by glass sides. The glass enclosure has aligned end-located ports so that the flow of urine does not encounter abrupt turns in the passage ways leading to the viewing chamber. The spacing between the flat sides is selected to provide a viewing chamber of even and optimum depth for microscope examination.

A holder is employed to receive and retain the glass enclosure while presenting a sufficiently low profile so as to enable use of the slide assembly with most conventional microscopes. The holder has metal tubes at end-located edges for connection to the ports of the glass enclosure and to appropriate flexible tubing to facilitate handling and mounting of the slide assembly.

With a slide assembly in accordance with the invention, problems encountered with other slide assemblies are avoided.

It is, therefore, an object of the invention to provide an apparatus and technique with which body fluids can be conveniently, safely, and expeditiously handled for analysis. It is a further object of the invention to provide a body fluid collection tube within which body fluids can be centrifuged and heavier components segregated and conveniently extracted in a consistent manner. It is still further an object of the invention to provide a slide assembly for use with a fluid examination apparatus of this invention and with which consistent microscope examinations can be carried out in a repetitive manner, with high reliability, in a safe manner, adaptable to various illuminating techniques such as phase contrast and Hoffman modulation, and useable with most microscopes at their respective magnification levels while using a small enough amount of test fluid to accommodate several examinations of the fluid from the same centrifuge tube.

These and other objects and advantages of the invention can be understood from the following detailed description of an apparatus and collection tube in accordance with the invention and as illustrated in the drawings.

BRIEF DESCRIPTION OF THE DRAWINGS

FIG. 4 is a front view in elevation of a urine sample collection and centrifuge tube in accordance with the invention;

FIG. 5 is a cross-sectional view of the collection tube shown in FIG. 4;

FIG. 6 is a bottom view of the collection tube of FIG. 5;

FIG. 7 is a partial, side cross-sectional view of the collection tube of FIG. 5;

FIG. 8 is a partial, front cross-sectional view of the collection tube as shown in FIG. 5 but in an inverted position;

FIG. 9 is a side cross-sectional view of a slide assembly for use with an apparatus as shown in FIG. 1;

FIG. 10 is another centrifuge and solids collection tube in accordance with the invention;

FIG. 11 is a partial longitudinal section view of the solids collection tube of FIG. 10;

FIG. 12 is a perspective view of a separator plug used in the collection tube of FIG. 10;

FIG. 13 is a cross-sectional view of the collection tube of FIG. 10 and is taken along the line 11—11 therein;

FIG. 14 is a cross-sectional downward view of a solids collection tube, without a separator plug, but modified in accordance with the invention;

FIG. 15 is a longitudinal cross-sectional view of the modified solids collection tube as shown in FIG. 14 and is taken along the lines 15—15 therein;

FIG. 16 is a perspective view of a modified separator plug for use in a collection tube as illustrated in FIG. 5;

DETAILED DESCRIPTION OF DRAWINGS

Figure 1:
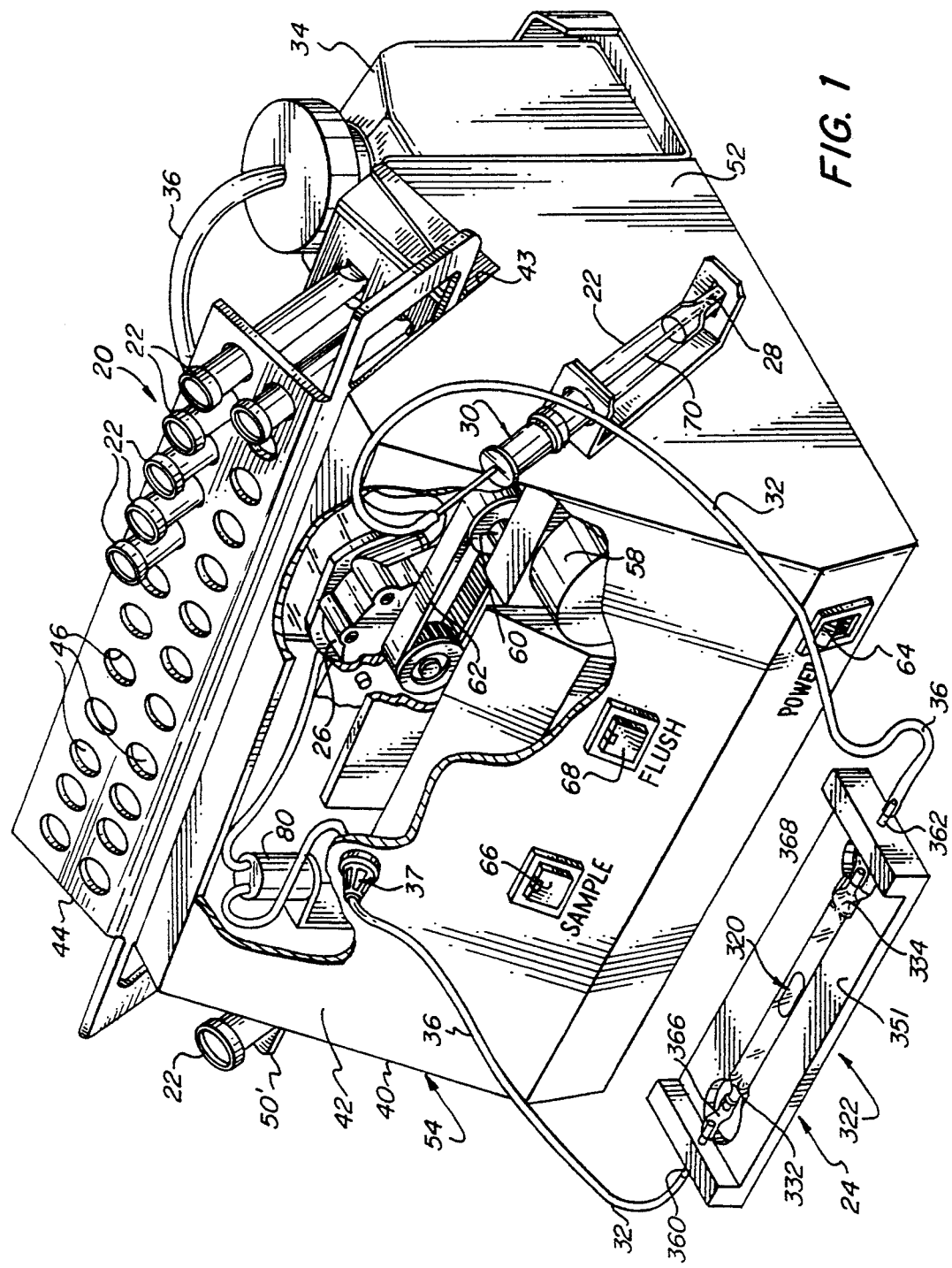
FIG. 1 is a front perspective, partially broken-away view of a body fluid handling apparatus in accordance with the invention.
Figure 2:
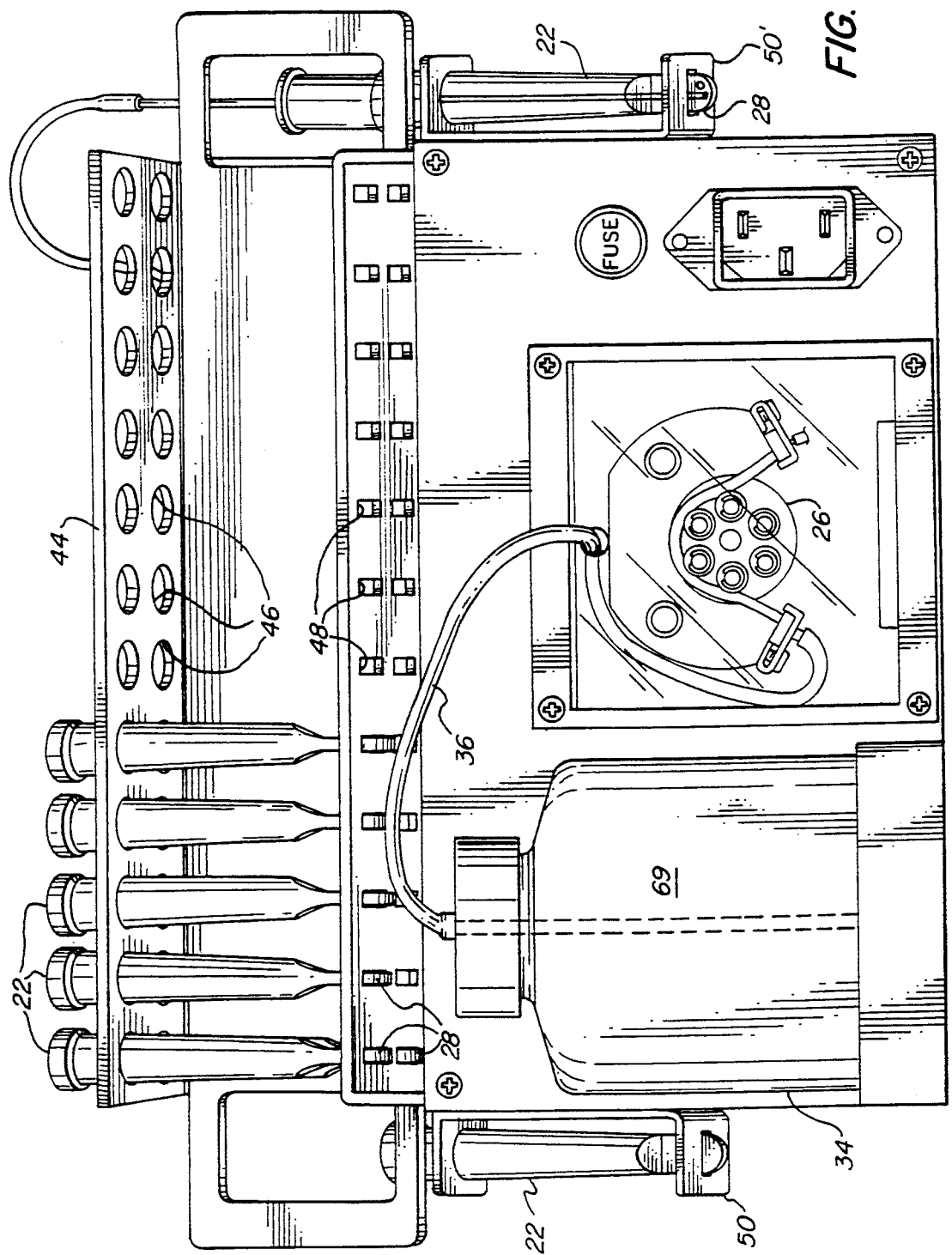
FIG. 2 is a rear view in elevation of the apparatus of FIG. 1.
Figure 3:
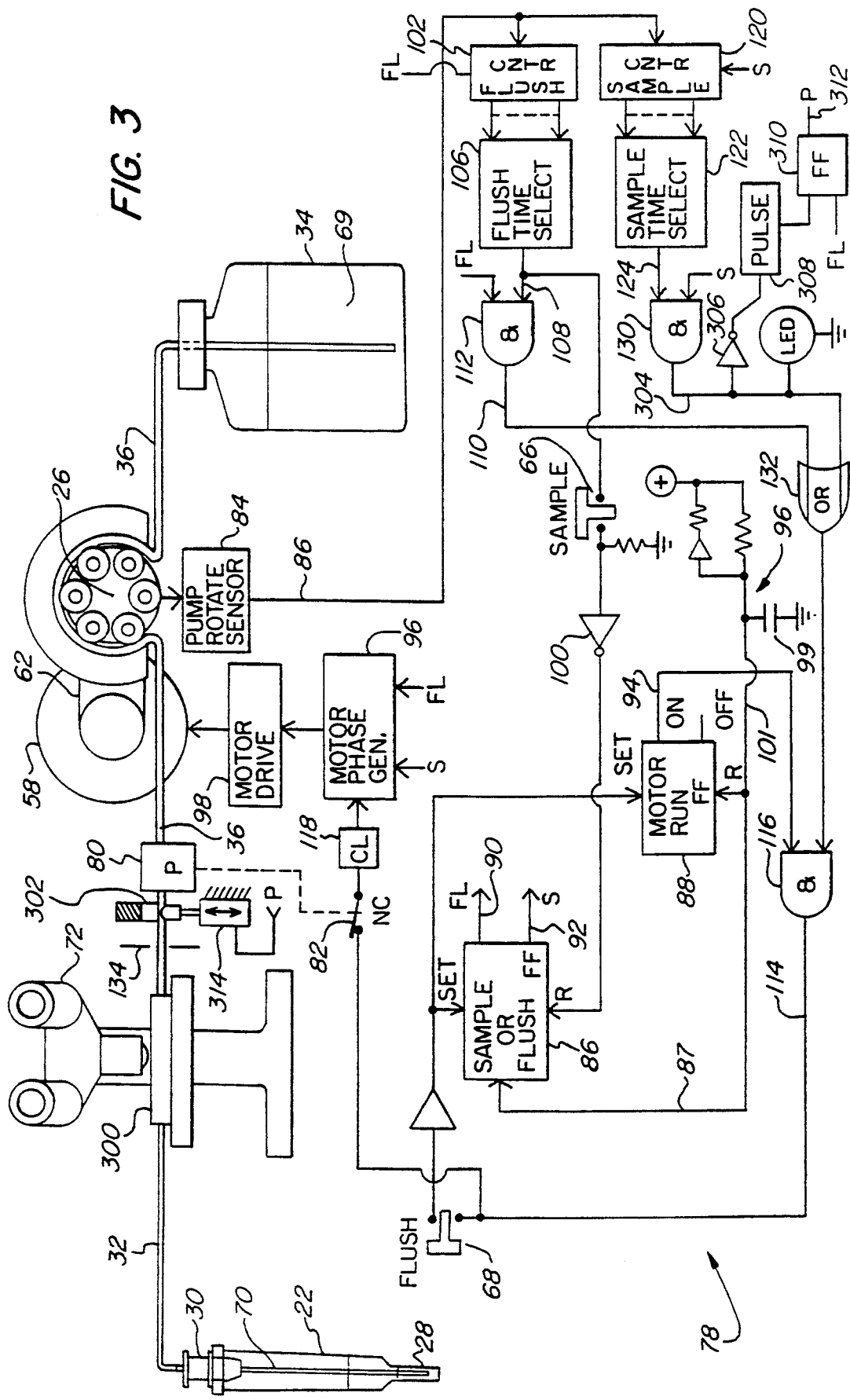
FIG. 3 is a block diagram and schematic view of the apparatus of FIG. 1.
Figure 17:
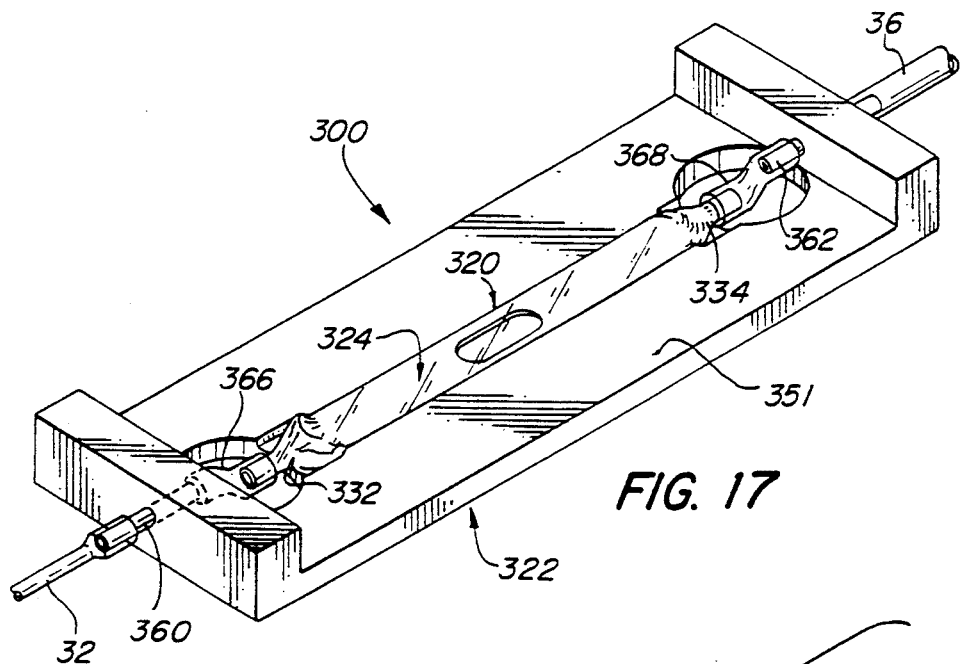
FIG. 17 is a perspective view of a slide assembly in accordance with the invention.
Figure 18:
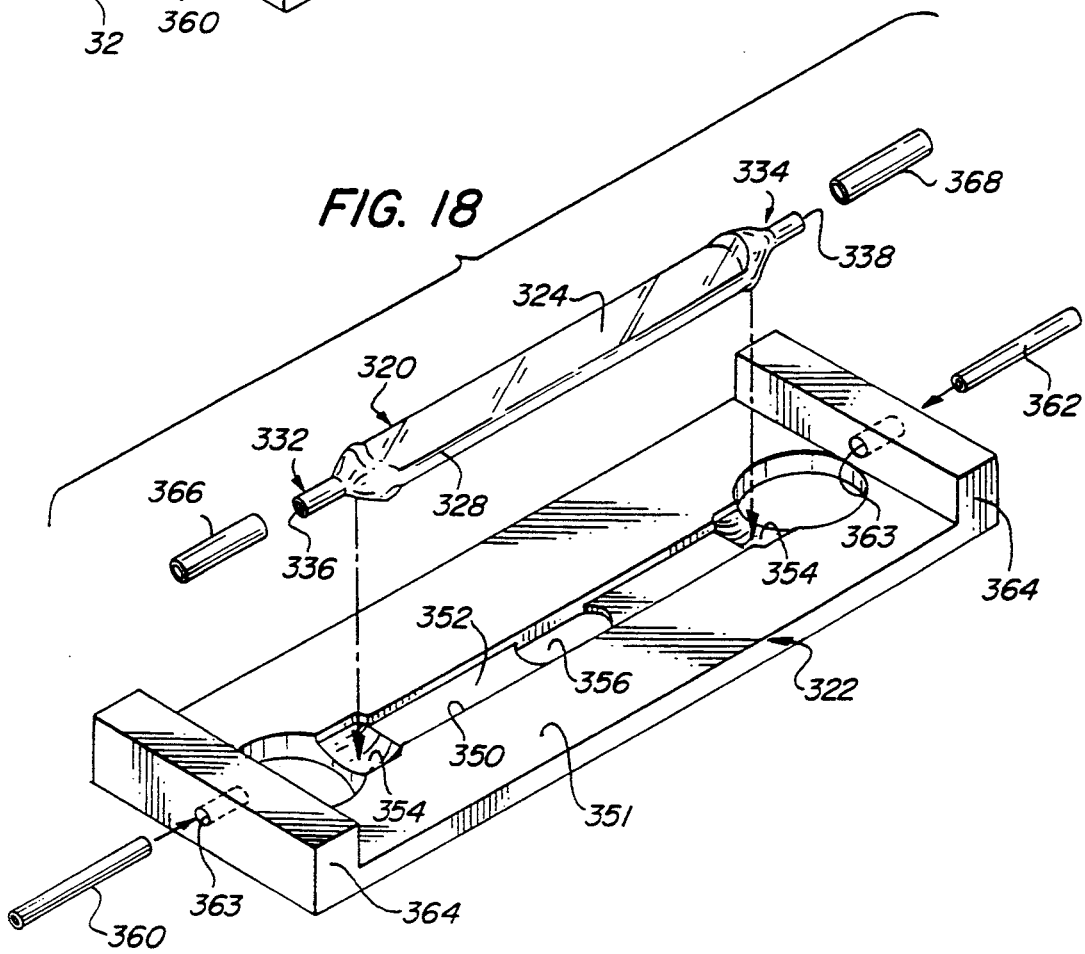
FIG. 18 is an exploded perspective view of the slide assembly of FIG. 18.
Figure 20:
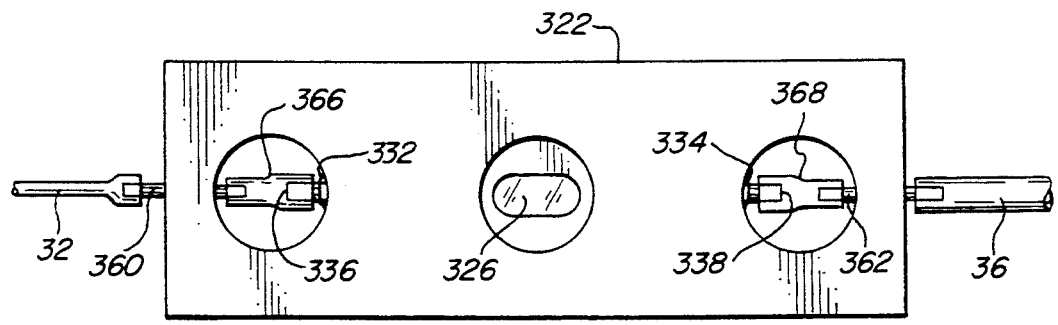
FIG. 20 is a bottom view of the slide assembly of FIG. 17.
Figure 19:
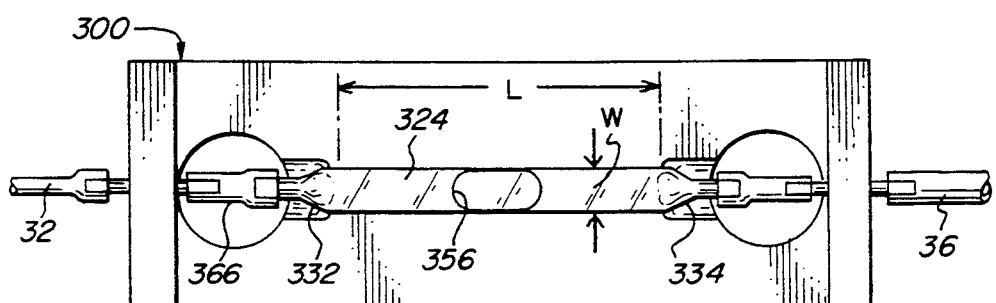
FIG. 19 is a top plan view of the slide assembly of FIG. 17.
Figure 21:
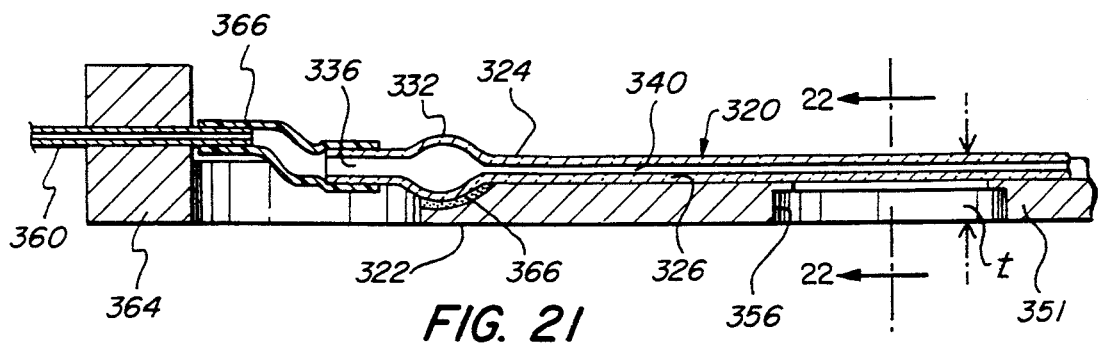
FIG. 21 is a partial enlarged section view of the slide assembly of FIG. 17.
Figure 22:
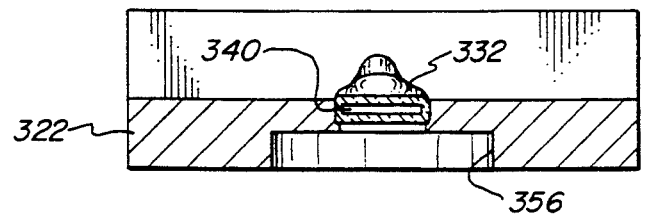
FIG. 22 is a section view of the slide assembly of FIG. 17 taken along the line 22—22 in FIG. 21.

With reference to FIGS. 1-3, an apparatus 20 is shown with which a urine sample is drawn from a collection and centrifuge tube 22 or such other centrifugable container as one may wish to use and pulled through a slide assembly 24. The apparatus 20 includes a peristaltic pump 26 which is reversible so that with one direction of rotation, a sample of urine is drawn from a solids collection chamber 28 in tube 22 through a probe assembly 30, and a flexible tube 32 into slide assembly 24. When the pump 26 is reversed, it draws a flushing liquid from a reservoir 34 and tubing 36 back to the collection tube 22. This is done for a sufficient length of time to flush the urine sample with its solids out of tubing 36, slide assembly 24, and tubing 32 and the probe assembly 30 into the collection tube 22. A quick connect-disconnect fitting 37, which is mounted on front panel 42, is interposed in tubing 36. This permits an easy replacement of slide assembly 24 and/or tubing 36 if severe contamination or damage occurs.

Preferably, a slide assembly 300 as illustrated in and described hereafter with reference to FIGS. 17-22 is employed with apparatus 20. The slide assembly 300 and tube 32 require a small amount of test fluid from collection tube 22. This is achieved by using a smaller cross-section tube 32 having an internal diameter bore in the range of about 0.021 inches while a larger tube 36, has an internal diameter bore of about 0.031 inches. This enables one to draw typically about one-half of the amount of test liquid available at the bottom end 28 of tube 22, thus leaving some for a repeat examination.

The apparatus 20 has a housing 40 with a sloped front panel 42 and a rack 44 on a top panel 43. The top panel is shaped to form a holding position for the stainless tube rack and cants forward for easy viewing. The rack 44 has a plurality of suitably-aligned apertures 46, 48 so as to stably retain a plurality of collection tubes 22. Single tube holding racks 50, 50' are located on side panels 52, 54 to, for example, enable the apparatus to be used in a left or right-handed mode.

Housing 40 further includes an electrically controlled reversible stepper motor 58 whose output shaft 60 is coupled by a belt drive 62 to rotate peristaltic pump 26. Housing 40 further includes a suitable power supply and electric circuitry as more particularly described with reference to FIG. 3.

In addition to a power control switch 64, the front panel 42 has pushbutton switches 66, 68 which respectively control the start of a sample handling and a flushing phase.

In the sample phase, a collection centrifuge tube, such as 22, contains a urine sample in lower solids collection chamber 28. The probe assembly includes an elongate hollow probe 70 which extends into chamber 28 and is connected to flexible tubing 32. As pushbutton 66 is actuated, the pump 26 is rotated in a direction and in an amount sufficient to pull a liquid sample through the probe 70 and slide assembly 24 but not so far as to enter the front panel on apparatus housing 40.

The slide assembly 300 which is mounted on a standard upright microscope 72, which hereinafter at times is referred to as a conventional microscope or just microscope, can then be optically examined.

When the examination is completed, the flush pushbutton 68 is actuated. This causes a reversal of the motor 58 in a direction whereby flushing liquid 69 is sucked from reservoir 34 and driven through tubings 36, and slide assembly 24, tubing 32, and probe assembly 30 10 into the collection tube 22.

The flushing actuation prepares slide assembly 24 and the connected tubings and probe for the next urine sample inside another collection tube 22. The entire process of handling of a urine sample for examination can be done in a short time and minimizes direct exposure by the operator to the body fluid.

In the event the first examination of a urine sample appears unacceptable, the flush cycle can be implemented but by discharging the sample and flushing liquid into another tube. The small sample needed for the first examination leaves enough residue for another sample to be drawn after reinserting the probe assembly 30 into the test tube containing the centrifuged urine.

FIG. 3 illustrates a control logic 78 used to operate apparatus 20. A pressure sensor 80 is placed in communication with flexible tubing 36 between fitting 37 and pump 26 to sense excessive pressures in the tubing such as may arise from a blocked probe 70 or an occluded tubing 32. A normally closed switch 82 is controlled by pressure sensor 80 and is located so as to interrupt drive to the motor 58. A pump rotation sensor 84 is used to generate pulses on line 86 representative of pump rotation and thus in effect representative of either the volume of sample liquid being drawn from collection tube 22 or the volume of flushing liquid 69 being pumped.

A pair of control flip-flops 86, 88 are employed to regulate the operation of pump 26. Flip flop 86 sets either sample or flush phases with its outputs 90, 92 respectively labeled S and FL. Flip flop 88 regulates the activation of reversible stepper motor 58 by way of "on" output 94.

The motor direction of rotation is controlled by a motor phase generator 96 which generates appropriately phased motor drive signals with a shift register enabled by the sample and flush phase signals S and FL. The motor phase signals are amplified by a motor drive 98.

The control 78 responds to a power on condition by forcing the phase control flip flop 86 into a flush mode and the motor run flip flop 88 in the OFF state. This can be achieved by a direct coupling with a line 87. A network 96 is provided and includes a capacitor 99 whose initial low voltage during turn-on assures that the motor run control flip flop 88 is in the OFF state. In this manner, the system must first activate a flushing operation before a sample can be drawn from a solids collection chamber 28 in tube 22.

When the flush control switch 68 is activated, the motor phase generator 96 generates appropriately phased pulses to stepper motor 58 to cause pump 26 to draw flushing liquid 69 from reservoir 34. As pump 26 rotates, sensor 84 generates pulses which are applied to a flush phase counter 102. A flush time selection network 106 is connected to counter 102 and generates, on output line 108 an enabling signal commensurate with the desired amount of flushing liquid to be pumped from reservoir 34 back into tube 22. Network 106 can be a decode network with dip switches to enable one to manually select the number of sensor pulses on line 86 needed to complete the flushing phase.

The output 108 from the flush select network 106 causes, in the flush phase, an output on line 110 from an AND gate 112 to in turn deliver a motor enabling signal on output 114 of gate 116 since the signal on line 94 was activated by flush control switch 68. The motor enabling signal is applied through pressure-control switch 82 to an enabling input of a clock 118 used to initiate the generation of motor drive pulses from motor phase generator 96.

If no excessive pressures occur in tubing 36, the motor 58 continues in its flushing direction until counter 102 reaches the count at which the flushing selection network 106 causes a cessation of the enabling signal on line 108. This removes the enabling signal to clock 118 and stops the motor 58.

At this time, the output on line 108 is in an active state for the sample control switch 66. Hence, when the sample push button 66 is activated, flip flop 86 is set in the sample mode. This enables a sample pulse counter 120 which counts pulses on line 86 from the pump rotation sensor 84.

The sample time selection network 122 produces an output on line 124 which acts through AND gate 130, OR gate 132, and gate 116 to energize clock 118. The sample phase generator 96 now produces pulses to drive motor 58 in a direction whereby pump 84 draws a sample from tube 22.

The duration of the sample rotation is controlled by the sample selection network 122. This is set, such as with dip switches, to extract a liquid sample from solids chamber 28 sufficient to extend through tubing 32 past slide assembly 24, but not so far as to reach the reservoir 34. Hence, preferably up to about a region indicated by line 134.

FIG. 9 illustrates a cross-section of the slide assembly 24. This includes a small volume transparent viewing chamber 140 which is adapted to enable viewing of a sample with the microscope as shown in FIG. 3. A preferred slide assembly 300 as shown in FIGS. 17–22 is used. Since but a small sample volume is drawn and differently-sized tubings 32 and 36 are employed, the flow from the test tube 22 tends to continue after the motor drive 98 has been stopped at the end of the sample phase. Since the flow tends to continue for some time, it is disturbing to the operator of microscope 72.

Hence, a solenoid actuated pinch valve 302 is used to pinch tube 36 between slide assembly 300 and pump 26. The valve 302 is actuated by a signal P generated at the end of the sample drawing by motor 62 and until the flush phase is begun. Signal P can be generated in various ways. One way may involve the signal at the output 304 of AND gate 130. This is applied to an output 304 of AND gate 130. This is applied to an inverter 306 whose output causes generation of a single pulse from a pulse generator 308. The output of pulse generator activates a flip-flop 310 whose output 312 goes active for the time period between the end of the sample phase and the end of the flush phase. The P signal on output 312 is then used to activate a solenoid 314 to close the pinch valve 302 and prevent further fluid flow though he viewing chamber of the slide assembly 300.

Another feature of the invention may involve use of a sample collection and centrifuge tube 22 with which a uniform sample can be conveniently obtained. This involves, as illustrated for one tube 22 of this invention in FIGS. 4–8, a sample collection tube 22 with a cylindrical upper body 144 and a transparent lower flattened body 146. The upper body encloses a chamber 148 which is separated from a lower-located solids collection chamber 28 by a plug 152. A bore 154 extends through plug 152 so that small solids can, during a centrifuge operation, pass through bore 154 into chamber 28.

Plug 152 is shaped so that it is seated in a fixed position between chambers 148, 28 at the transition section 156 of tube 22. The upper portion 158 of plug 152 has a larger cross-section than its lower portion 160 which extends slightly into chamber 28. The through bore 154 terminates at portion 160 which is shaped to form a valve seat 162 for a freely-moving small ball valve 164 which is captured within chamber 28. Valve seat 162 can be concave or V-shaped or such other shape as is desirable to form a valve seat. Ball valve 164 has a specific gravity that is sufficiently high so as not to float inside chamber 28 and thus normally rest on the bottom of chamber 28. For urine collection and centrifuge, a specific gravity greater than one is needed.

During a centrifuge operation, the probe assembly 30 is not present. The solids in the urine specimen are forced through bore 154 into the lower chamber 28. At the end of the centrifuge, excess liquid is in the upper chamber 148 and solids have aggregated into a consolidated mass in the lower chamber 28. The excess liquid in the upper chamber can be decanted, without loss of liquid from the lower chamber 28, by sufficiently inverting the tube 22, as illustrated in FIG. 8. This shows the ball valve on the valve seat 162, resulting in the retention of a fixed volume of liquid in chamber 28.

When tube 22 is placed upright again, ball valve 164, which has a sufficient mass, can be used with a gentle agitation of tube 22, to break up any consolidated solids in mass 170 and cause them to be resuspended. Since the resuspension occurs within a consistent volume of liquid inside chamber 28, the density of solids can be more accurately determined from the microscopic investigation.

During a centrifuge operation, solids tend to collect at the small ledge formed between the upper edge 172 of the plug 152 and the inner wall 174 of upper chamber 148. Hence, as shown in FIG. 16 in a preferred form of a plug 152', its upper edge 172 is made as small as possible and is spaced away from wall 174 by use of longitudinally-extending ribs 176. These ribs provide thin, capillary-sized, passages 178 around the periphery of plug 152. Passages 178 are sufficiently wide to allow solids to pass through to the collection chamber 28, yet not so wide as to allow liquid to escape when the excess liquid in chamber 148 needs to be decanted.

FIGS. 10–13 illustrate another centrifuge and solids collection tube 180. The tube 180 can be of conventional shape with a wide upper body 182 and a conical lower body 184. A plug 186 is provided with an upper portion 188 shaped to snugly fit inside the upper body 182 and a lower portion 190 that extends slightly into the lower body 184. Ribs 192 extend along the outer surface of plug 186 to form capillary-sized passages 194 between the ribs for passage of centrifuged solids.

Plug 186 has a through bore 196 and valve seat 198 facing a solids collection chamber 200. A ball valve 164' is located in chamber 200.

In an alternate form of a solids collection tube in accordance with the invention as shown in FIGS. 14 and 15, ribs 202 similar to ribs 176 in FIG. 16 or 192 in FIG. 12 are placed on the inside wall 174' of tube 180. The ribs are integrally molded with the tube 180 by adding appropriately-shaped recesses to an injection molding die used to make tubes such as 180. The spaces 204 between ribs 202 then form, with an appropriately outer smooth-walled plug such as 186 desired longitudinal capillary passages.

With reference to FIGS. 17–22, the preferred slide assembly 300 is shown formed of a transparent elongate optical glass enclosure 320 mounted to a metal slide support 322. The optical enclosure 320 is made from a preform glass extrusion with flat upper and lower transparent slide walls 324, 326 and sides 328, 330. The enclosure ends 332, 334 are formed into short tubes to provide end-located ports 336,338 in alignment with an elongate-viewing chamber 340.

The optical glass enclosure has an evenly thick capillary-sized viewing chamber 340 whose width, w, is commensurate with that needed to enable an optical examination of a fluid with microscope 72. The dimensions of the optical glass enclosure are selected commensurate with good viewing through a microscope into the fluid. This involves a thickness of each slide wall 324, 326 of about 0.007 inches±ten percent and a thickness of the viewing chamber of about 0.005 inches±five percent.

The slide support 322 has a central elongate recess 350 in a midsection 351 and which is sized to freely yet snugly receive the elongate optical glass enclosure with its lower wall 326 facing the bottom 352 of recess 350. The ends 354 of recess 350 are shaped to receive ends 332, 334 of glass enclosure 324. Recess 350 has a cut-out 356 to allow light to pass through from below during microscope viewing. A pair of stainless steel tubes 360, 362 are mounted inside bores 363 formed in end 364 of holder 322 and serve to form a fluid flow connection with flexible tubings 32, 36 (see FIGS. 1 and 3). Flexible tubes 366, 368 are used to connect tubular ends 332 and 334 to stainless steel tubes 360, 362. The optical glass enclosure 324 is cemented in place inside recess 350 with the use of a suitable adhesive 366 as may be applied at ends 354 of recess 350. The end walls 364 protrude above the midsection 351 and spaced sufficiently far apart so as to avoid interference with a microscope focused on the viewing chamber.

An important feature of slide assembly 300 is its useability on virtually most microscopes used in clinical laboratories where urinalysis is done. The maximum thickness profile, t, within the operational range of the microscope is, therefore, limited to as small as is reasonably practical. Generally, the thickness profile t is of the order of less than about three millimeters while still being able to draw a fluid sample from collection tube 22 and accommodate a flushing cycle as described. The depth of recess 350 is selected to receive most of the glass enclosure 320 with a small protrusion above the surface 370 of the central segment 372 of the holder 322 to enable a close approach of the slide assembly 300 by the lens of a microscope.

Since some thickness increase is required at the ends 332, 334, the overall length L of the flat segment of the glass enclosure 320 is made sufficiently long to avoid interference between the microscope and the glass enclosure 320. This length may vary, but generally about one and a half inches has been found to be satisfactory.

With a slide assembly 300, the operation of a urinalysis is considerably improved. The small volume of the viewing chamber 340, of the order of generally less than about thirty microliters, and the use of a small diameter bore for the flexible tube 32 limits the amount of fluid needed for a sample. With the alignment of the ports 336, 338 with the elongate viewing chamber, abrupt turns are avoided, thus reducing the formation of tiny bubbles and avoiding a lodging of particles and bacteria because these are now easier to flush out. By using glass extrusion for the enclosure 320, cement interfaces are avoided and microscope viewing is enhanced and various known illumination techniques can be used.

Having thus described illustrative forms of the invention, its advantages can be appreciated. Variations from the described embodiment can be made without departing from the scope of the invention.

What is claimed is:

1. An apparatus for drawing a sample of test fluid inside a container through a slide assembly for analysis with a microscope comprising:

a flushing fluid supply;

pump means for pumping fluid between the container and said flushing fluid supply;

reusable slide means having a viewing chamber for holding a fluid sample for direct viewing of the fluid sample by the microscope; said reusable slide means being removably mountable to the microscope; said reusable slide means including an elongate optical glass enclosure having upper and lower substantially flat walls spaced-apart from each other to form an elongate viewing chamber with the spacing between the substantially flat walls being commensurate with that required for said test fluid to move into the viewing chamber for effective viewing with the microscope for test fluid analysis;

said elongate optical glass enclosure having integral end-located glass ports which are generally in longitudinal alignment with the elongate viewing chamber so as to present smooth passage to the flow of fluid;

flexible tubing means for establishing fluid flow communication between the container and said reusable slide means and between the reusable slide means and said pump means;

means for activating the pump means in one operative direction for a sufficient time so as to draw a sample of test fluid from the container through the viewing chamber of the glass enclosure without passing into the flushing fluid supply;

means for activating the pump means in another operative direction for pumping flushing fluid from the flushing fluid supply through the viewing chamber to flush the test fluid sample therefrom into said container.

2. The apparatus as claimed in claim 1 wherein said reusable slide means has, at said viewing chamber, an overall thickness which extends over a desired length and is selected so that said reusable slide means operates with microscopes used in urinalysis.

3. The apparatus as claimed in claim 2 wherein said overall thickness is of the order of generally less than about three millimeters.

4. The apparatus as claimed in claim 2 wherein said reusable slide means includes an elongate support, said elongate support having a midsection; said midsection having an elongate recess bounded by elongate walls and being sized and shaped to receive freely without interference and adjacent to said elongate walls said elongate optical glass enclosure; said midsection having a slot located in alignment with the viewing chamber of the elongate optical glass enclosure.

5. The apparatus as claimed in claim 4 wherein said elongate support has end walls extending above said midsection, said end walls being sufficiently spaced from each other to avoid interference with the operation of a microscope focused on the viewing chamber, said end walls further having tubes extending therethrough which are in fluid flow communication with the glass ports of said elongate optical glass enclosure and with said flexible tubing means.

6. The apparatus as claimed in claim 5 wherein the thickness profile of the midsection and the elongate optical glass enclosure is generally less than about three millimeters.

7. The apparatus as claimed in claim 1 and further comprising a said container wherein said container comprises:
a tube having a wall, a closed end, and an open end, said tube being shaped for a centrifuge operation during which solids inside a fluid held within the tube tend to collect adjacent the closed end;
a plug inside the tube and seated in fixed spaced relationship from the closed end to define a solids collection chamber having a constant volume between the plug and the closed end, said plug having a bore extending therethrough and terminating with a valve seat facing the solids collection chamber, the cross-section of the bore being sized for solids in the fluid to pass through and pass a sample removing probe; and
a loose valve element formed of a material having a specific gravity sufficiently high so as not to float on the test fluid and located within the solids collection chamber, said loose valve element being sized to fit on the valve seat to seal the bore of the plug when the tube is inverted to decant excess fluid so as to preserve a substantially known amount of sample fluid within the solids collection chamber, said loose valve element having sufficient mass to break-up aggregated solids as these were consolidated from a centrifuge operation.

8. A reusable slide assembly for use in urinalysis with a microscope, comprising:
an elongate transparent extruded glass seamless enclosure having elongate upper and lower transparent planar walls which are spaced from each other to form an elongate viewing chamber for use with a microscope, said elongate upper and lower transparent planar walls being spaced by a distance commensurate with a spacing as encountered between a cover slip and a glass slide used in conventional microscope urinalysis;
said elongate transparent extruded glass seamless enclosure terminating at opposite ends at first and second glass ports which are in longitudinal alignment with the elongate viewing chamber to provide a smooth entry and exit of fluid to and from the elongate viewing chamber and are an integral part of the glass enclosure;
an elongate holder having a midsection on which the elongate transparent extruded glass seamless enclosure is mounted with a said wall facing the midsection, said holder midsection further having a light passing opening located in viewing alignment with the elongate viewing chamber of the elongate transparent extruded glass seamless enclosure;
said elongate holder further having first and second tubes mounted to opposite ends of the holder in general longitudinal alignment with the first and second glass ports of the elongate transparent extruded glass seamless enclosure and being in fluid flow communication with said first and second glass ports of the elongate transparent extruded glass seamless enclosure.

9. The reusable slide assembly as claimed in claim 8 wherein the glass enclosure is formed from an extruded preform and wherein the overall thickness profile of the holder midsection and the glass enclosure mounted thereon is selected so that said slide assembly operatively fits beneath microscopes used in urinalysis.

10. The reusable slide assembly as claimed in claim 9 wherein said overall thickness profile is generally less than about three millimeters.

11. The reusable slide assembly as claimed in claim 9 wherein the length of said elongate transparent extruded glass seamless enclosure is selected so that said overall thickness profile extends over a distance selected to avoid interference with the operation of a microscope focused on the elongate viewing chamber.

12. The reusable slide assembly as claimed in claim 8 wherein said midsection has a recess bounded by a wall and being sized to receive, freely without interference, and adjacent to said recess wall, the glass enclosure, said midsection having an opening therein in alignment with the viewing chamber of the glass enclosure for illumination of test fluid within the viewing chamber.

13. The reusable slide assembly as claimed in claim 12 wherein the depth of said recess is selected so that the elongate upper wall of the elongate transparent extruded glass seamless enclosure protrudes above the midsection.

14. The reusable slide assembly as claimed in claim 12 wherein the elongate holder has end walls extending upwardly above the midsection, with said first and second tubes mounted in said end walls and being in fluid flow communication with the glass ports of the elongate transparent extruded glass seamless enclosure.

15. The reusable slide assembly as claimed in claim 14 wherein said end walls are sufficiently far apart so as to avoid interference with the operation of a microscope focused on the viewing chamber.

16. A fluid collection tube, comprising:
a tube having a wall, a closed end, and an open end, said tube being shaped for a centrifuge operation during which solids inside a fluid held within the tube tend to collect adjacent the closed end;

a plug inside the tube and seated in fixed spaced relationship from the closed end to define a solids collection chamber having a constant volume between the plug and the closed end, said plug having a bore extending therethrough and terminating with a valve seat facing the solids collection chamber, the cross-section of the bore being sized so that solids in the fluid pass through the bore from a region above the plug to the solids collection chamber and pass a sample removing probe; and a loose valve element formed of a material having a specific gravity selected so as not to float in the fluid and located within the solids collection chamber, said loose valve element being sized to fit on the valve seat to seal the bore of the plug when the tube is inverted to decant excess fluid so as to preserve a substantially known amount of sample fluid within the solids collection chamber, said valve element having sufficient mass to break-up aggregated solids as these were consolidated from a centrifuge operation.

17. The fluid collection tube as claimed in claim 16 wherein the plug has an outer peripheral wall contacting the wall of the tube, and a plurality of fluid passages located between the outer peripheral wall of the plug and the tube wall and being in communication with the solids collection chamber and the region above the plug, said plurality of fluid passages being sized to enable solids to pass therethrough during a centrifuge operation while inhibiting escape of fluid when the tube is inverted.

18. The fluid collection tube as claimed in claim 17 wherein the tube is provided with a plurality of circumferentially spaced inwardly protruding ribs opposite the plug, the ribs being sized so that circumferential spaces between the ribs form said plurality of fluid passages.

19. The fluid collection tube as claimed in claim 17 wherein the outer peripheral wall has a plurality of circumferentially-spaced, outwardly projecting ribs to seat against the tube wall, the ribs being sized so that circumferential spaces between the ribs form said plurality of fluid passages.

20. The fluid collection tube as claimed in claim 16 wherein the tube wall has a cross-section transition zone with a generally cylindrical upper part above the cross-section transition zone and a reduced cross-section lower part below the cross-section transition zone; and wherein the plug has an upper portion and a lower portion, said upper portion being generally cylindrical in shape to fit close to the upper part of the tube wall, said lower portion being commensurately-shaped as said transition zone so that said plug is firmly seated in a fixed position against the tube wall at the transition zone during a centrifuge operation.

21. The fluid collection tube as claimed in claim 20 wherein the reduced cross-section lower part has generally flat, spaced-apart opposing end walls, the spacing between said generally flat, spaced-apart opposing end walls being less than the diameter of the generally cylindrical upper part.

22. The fluid collection tube as claimed in claim 20 wherein the reduced cross-section lower part is generally conically-shaped and wherein the lower portion of the plug has a conically-shaped peripheral surface sized so as to seat against the reduced cross-section lower part of the tube wall.

23. The fluid collection tube as claimed in claim 16 wherein the plug has an upper rim and a funnel-shaped recess extending from the upper rim and terminating at an entrance port of the bore so as to guide solids to the solids collection chamber during a centrifuge operation.

24. The fluid collection tube as claimed in claim 23 wherein the plug has an outer peripheral surface and a plurality of circumferentially-spaced, downwardly-extending elongate ribs, said ribs being sized so as to space the upper rim from the tube wall to reduce a pile up of solids on the upper rim.

* * * * *